United States Patent [19]

Dole et al.

[11] Patent Number: 4,859,603
[45] Date of Patent: Aug. 22, 1989

[54] PERSONAL DIAGNOSTIC KIT

[75] Inventors: Charles M. Dole, Purdys, N.Y.; Gary L. Webster, Fairfield, Conn.

[73] Assignee: Dole Associates, Inc., Katonah, N.Y.

[21] Appl. No.: 196,666

[22] Filed: May 20, 1988

Related U.S. Application Data

[63] Continuation of Ser. No. 439, Jan. 5, 1987, Pat. No. 4,769,333.

[51] Int. Cl.$^4$ .................. C12M 1/00; B01L 11/00
[52] U.S. Cl. .................. 435/287; 435/810; 436/808; 422/56; 422/61; 422/101; 222/83
[58] Field of Search ............. 435/7, 810, 287, 299, 435/300, 301, 311; 422/56, 57, 58, 61, 68, 101, 102; 436/808, 809, 65, 610; 222/83, 81; 206/569, 603

[56] References Cited

U.S. PATENT DOCUMENTS

| | | | |
|---|---|---|---|
| 3,355,069 | 11/1967 | Miles | 222/486 |
| 3,657,073 | 4/1972 | Burton et al. | 435/291 |
| 3,689,224 | 9/1972 | Agnew et al. | 422/61 |
| 3,776,220 | 12/1973 | Monaghan | 435/295 |
| 3,799,742 | 3/1974 | Coleman | 422/61 |
| 3,986,834 | 10/1976 | Steinbrink, Jr. | 422/61 |
| 4,246,339 | 1/1981 | Cole et al. | 435/287 |
| 4,324,758 | 4/1982 | Eisentraut et al. | 222/144 |
| 4,366,241 | 12/1982 | Tom et al. | 435/7 |
| 4,428,506 | 1/1984 | Withey | 222/83 |
| 4,428,907 | 1/1984 | Heijenga et al. | 422/83 |
| 4,458,020 | 7/1984 | Bohn et al. | 435/287 |
| 4,549,655 | 10/1985 | Forsythe, Jr. et al. | 422/58 |
| 4,632,901 | 12/1986 | Valkirs et al. | 435/287 |
| 4,665,034 | 5/1987 | Chandler | 435/287 |

Primary Examiner—Randall L. Green
Assistant Examiner—Denise L. Ferensic
Attorney, Agent, or Firm—Bachman & LaPointe

[57] ABSTRACT

A personal, disposable hand held diagnostic kit having a specimen support member such as a membrane, wafer on the like including a plurality of liquid receptacles with means for applying the liquids to said support member in sequence for relatively immediate observation of reaction and ultimate diagnosis.

6 Claims, 2 Drawing Sheets

PERSONAL DIAGNOSTIC KIT

This is a continuation of application Serial No. 000,439 filed Jan. 5, 1987 now U.S. Patent No. 4,769,333.

BACKGROUND OF THE INVENTION

The present invention relates to assay or diagnostic kits and relates in particular to disposable, hand held kits useful to make relatively immediate tests, assays or diagnoses, personally.

Typical prior art devices are disclosed in U.S. Patent Nos. 3,986,834, 4,162,003, 4,175,008, 4,549,655, and 4,608,231.

The '834 patent shows a series of reagent bottles 14 received in a tray 12 where the bottles contain a frangible capsule 20.

The '003 patent shows a plurality of bottles 1 and 6 having a separate compartment 5.

The '008 patent shows a specimen collector and transport test tube 10.

The '655 patent shows relatively rotatable elements 14 and 16 for registering openings 20 and 34 with layered stack 12.

The '231 patent shows a bracket unit 10 for supporting a plurality wells such as well 14.

SUMMARY OF THE INVENTION

In contrast the present invention deals with a compact, hand held, disposable assay, test or diagnostic kit which is very easy to operate and produces meaningful results in rapid fashion.

It is a further feature of the invention to provide a composite test kit whose size and configuration lends itself economically to modern high speed mass production methods using appropriate synthetic moldable compounds.

A further feature of the invention is the provision of a kit of the type described which includes a plurality of receptacles for containing fluid reagents or other liquid materials including water with means for releasing fluids selectively to react upon a test specimen.

A further feature of the invention is the provision of a diagnostic, assay or test kit which, by virtue of its structure, is operable to perform a number of useful functions providing results that are meaningful to the ordinary layman.

A still further feature of the present invention is the provision of a kit of the type described which is self contained whose operation is performed personally by the user without the need for technical or professional supervision or assistance.

A further feature of the invention is that groups of kits can be "loaded" or charged at the point of manufacture where each group is designated to perform a specific test, assay or diagnosis.

For example, one group of kits may be available commercially as a pregnancy test.

Another group of kits may be charged with reagents or fluid materials for identifying the existence of particular bacteria, virus, or other identifiable material.

A further feature of the invention is the provision of a novel arrangement or array of receptacles for containing liquid materials where means are provided for releasing said liquids sequentially for reaction with a test specimen where all liquid materials are contained at all times within the kit in a neat and tidy fashion.

A diagnostic kit embracing certain principles of the invention may comprise a support member for suspending at least one receptacle containing liquid material and a cutting element operatively connected to said support member, said support member and said cutting element being movable relative to one another whereby said cutting element is operable to shear or slit said receptacle to release said liquid material from said receptacle to rain or play upon a test specimen when said relative motion occurs.

BRIEF DESCRIPTION OF THE DRAWINGS

Other features and advantages of the present invention will become more apparent from an examination of the succeeding specification when read in conjunction with the appended drawings, in which.

DETAILED DESCRIPTION OF THE INVENTION

Figure 1:
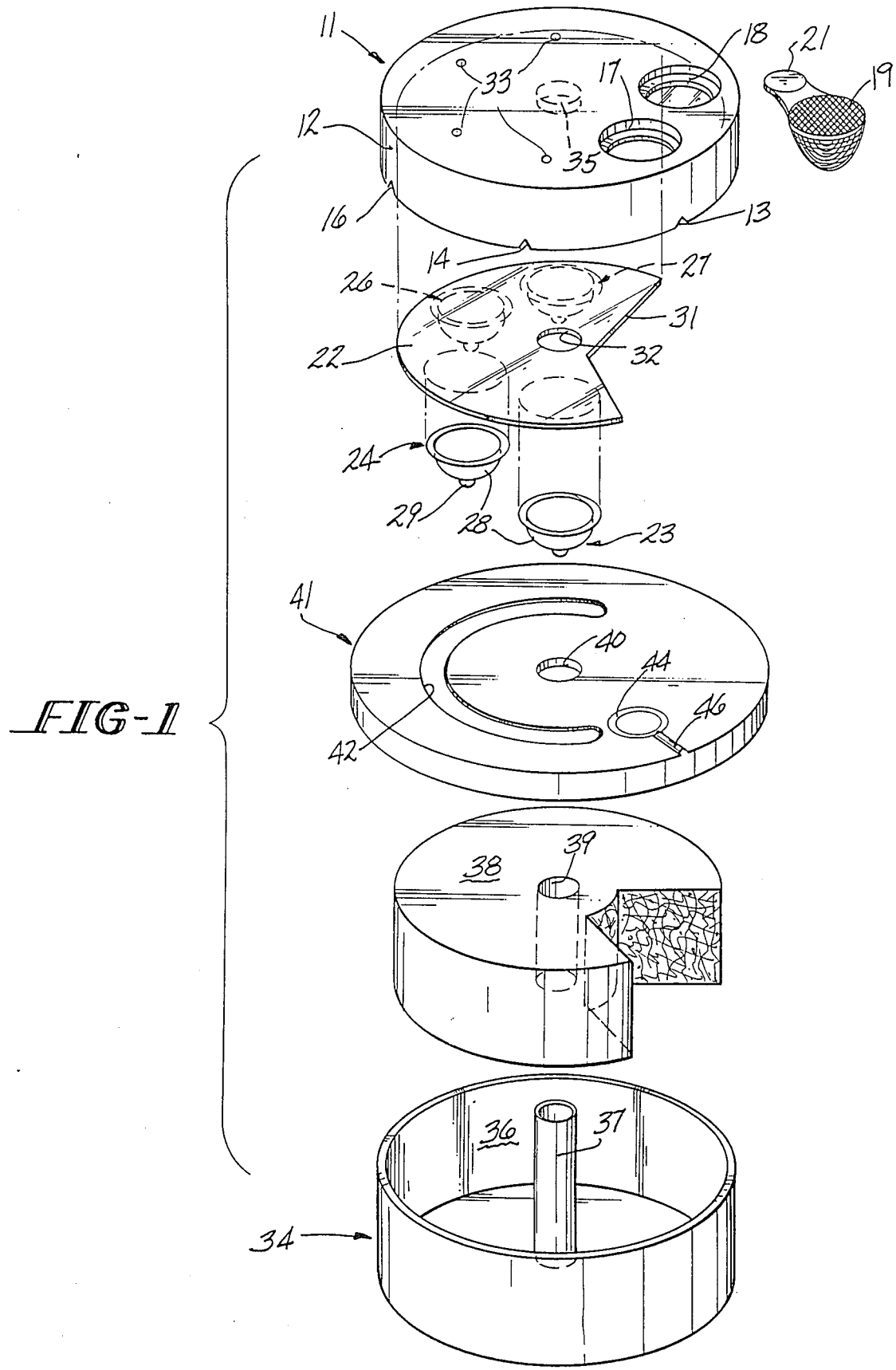
FIG. 1 is an exploded view of the basic elements of the kit of the present invention.

Referring in detail to FIG. 1, a first housing member 11 formed with a skirt 12 having V-shaped notches 13, 14, and 16 (first detent means) is further formed with a specimen access opening 17 and a viewing access opening 18. The specimen access opening 17 is operable to receive a funnel-filter 19 having a finger tab 21 in the event a test specimen introduced into opening 17 contains solid or agglomerate matter which must be retained or removed.

Below the first housing member 11 is circular sector 22 which serves as a support member (first support means) for a plurality of liquid tight containers or receptacles 23, 24, 26, and 27 having a body portion 28 and a nipple portion or protuberance 29.

The sector 22 includes a cut-out 31 and a central operative 32 whose purpose and function will become more apparent as the specification proceeds.

The receptacles 23 through 27 fabricated or molded of a suitable light gauge synthetic plastic which cuts or shears readily, are filled with liquid materials appropriate to the particular test, array, or diagnostic and are secured to the underside of the sector 22 by a suitable adhesive or by high frequency heating, as desired.

The sector 22 and the suspended liquid receptacles 23 through 27 are secured to the underside of the first housing member 11 in suitable fashion.

It is well to note this juncture that in some embodiments of the invention the sector 22 may be eliminated and the liquid receptacles 23 through 27 are secured directly to the underside of the first housing member 11. Thus, the underside of the housing member 11 becomes the receptacle support member. In this event the housing member 11 may be provided with small sealable access openings as indicated by circles 33-33 for loading or changing the receptacles using an appropriate syringe device.

Alternatively, the receptacles may be formed as a group (vacuum formed, for example) from a sheet of suitable plastic material where all receptacles are joined or are interconnected by margins between receptacles. After filling each receptacle with the material appropriate to the test, a sealing film is placed over the formed sheet covering and sealing each receptacle and the margins.

Thereafter, the formed, filled, and sealed sheet is secured by suitable means to the underside of the first housing member.

A second housing member 34 having an upstanding skirt 36 formed with a central pin or axle 37 receives an absorbant pad 38 having a clearance opening 39 for the axle 37.

The axle, providing a central bearing for a rotary cutting element 41 passes through aperture 40 and aperture 32 of sector 22 and bottoms in an internal socket 35 in first housing member 11. The axle is fixed to the housing member 11 by appropriate means with adequate clearance to permit relative motion between the cutting element 41 (second support means) and the assembled first and second housing members in a manner and for a purpose that will become apparent hereinafter.

The cutting element 41 is shaped in the form of a disc of a diameter somewhat larger the the diameter of the housing members and is knurled or roughened at its periphery to facilitate grasping manually.

Figure 3:
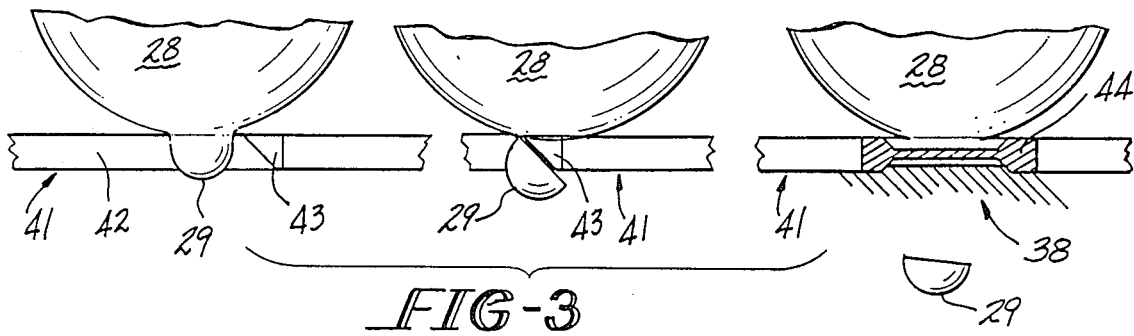
FIG. 3 is a schematic illustration of the rotary disc its cutting element, the shearing sequences and the test specimen support element or wafer.

The cutting element or disc 41 is formed with a through slot 42 of an arcuate configuration complementary to the arcuate array of the nipples 29 of the receptacles 23, 24, 26, and 27. The slot 42 receives and provides clearance for the nipples 29 as is most apparent in FIG. 3.

The right extremity of the slot terminates in a knife or cutting edge 43 and immediately adjacent the cutting edge is a support element 44 for receiving a test specimen. The specimen support element 44 may take the form of a wafer, a membrane including a permeable or treated membrane as test, assay or diagnostic procedures require.

The cutting element or disc 41 is formed further with a rib or detent 46 (second detent means) projecting radially and centrally from the specimen support element 44. The detent 46 cooperates with notch 13 of first housing member 11 (aligned with specimen access opening 17) to lock the disc 41 releaseably with the specimen access opening 17 in register with the specimen support element 44. The viewing access opening 28 is also provided with a detent means (not shown).

Figure 2:
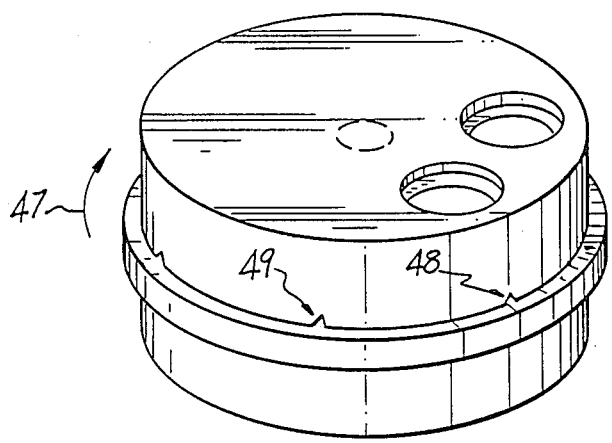
FIG. 2 is a perspective view of the assembled kit.

Operation of the kit occurs as follows:

Assume that the device is assembled as shown in FIG. 2 with the specimen access opening 17 in releasable register with the specimen support element 44 and with the several receptacles 23, 24, 26, and 27 having been charged or loaded at the point of manufacture with liquid material appropriate to the test, assay or diagnosis for which the kit is intended. In addition, assume that the specimen support element 44 has been inoculated or coated with a specimen by the user (consumer) using filter-funnel 19 or swab 52 and swab holder 51, as appropriate.

At this time the nipples are received in the arcuate slot 42 clear of the knife 43.

The individual user grasps the housing firmly (the first housing member 11 or the second housing member 34 or both members) and rotates the disc 41, in the direction of the arrow 47 of FIG. 2, relative to the housing.

This occurrence breaks or releass the detent lock at 48 FIG. 2 and the disc 41 and its detent 46 are moved relative to the housing until the detent 46 snaps into the next housing notch at 49.

During the course of this relative rotation the knife 43 operates to shear nipple 29 (see FIG. 3) from its mating receptacle 28 to release fluid material. The location of detent means (notch at 49) on the skirt 12 of the first housing member insures that the material released rains or plays upon the test specimen as shown on FIG. 3.

Absorbant pad 38 is of sufficient thickness to wipe the underside of the disc 41 to absorb any excess fluid material.

After an appropriate interval and in accordance with kit instructions the disc 41 is rotated to the next detent lock, a nipple is sheared, and the test specimen is again showered with liquid material from a second receptacle.

Obviously the number of receptacles 23, 24, 26, and 27 is not critical to the present invention, so long as there are sufficient reagents including water available for the particular test, assay or diagnosis for which the kit is intended.

It is also well to point out that although the relative motion described in connection with the exemplary embodiment of the invention is rotary it is entirely within the spirit and scope of the invention that the relative motion be linear (reciprocal, for example) or part rotary and part linear so long as relative motion between the knife and the receptacles operates to slit receptacles sequentially to release liquid to treat a test specimen.

Figure 4:
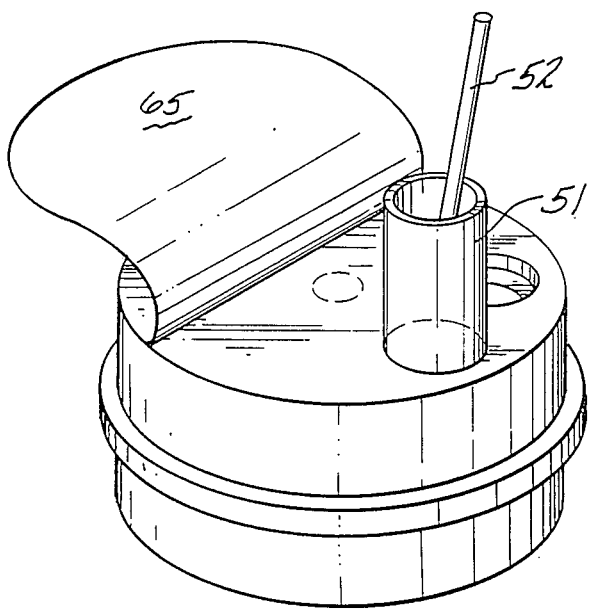
FIG. 4 is a perspective illustration of the assembled kit showing a swab and swab holder for introducing a test specimen to said specimen support element of FIG. 3, and, FIG. 5 is a schematic illustration of a liquid receptacle containing a capsule-like secondary liquid container including a needle-like probe for puncturing said secondary container to release its liquid.

FIG. 4 shows an alternative scheme for introducing a test specimen to specimen support element 44 in that swab holder 51 and a swab 52 are used in lieu of in the funnel-filter 19 of FIG. 1. FIG. 4 also shows a releasable foil or film 65 for sealing the first housing member 11, at the point of manufacture, to close all openings 17, 18 and 33, as required.

Frequently it is desirable to intermix two different liquid materials just prior to personal use of the kit. These are situations where, for example, premature co-mingling of liquids would reduce or eliminate their efficacy.

Figure 5:
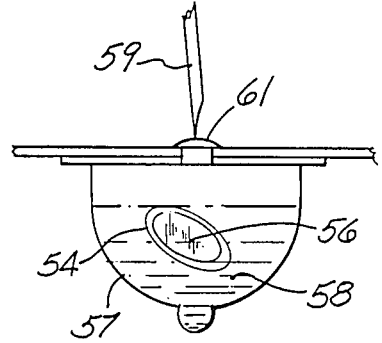

In such situations arrangements such as shown in FIG. 5 are devised. A soft pliable capsule 54 containing a fluid material 56 is disposed in a selected receptacle 57 containing fluid material 58.

At the appointed time prior to personal use of the kit and in accordance with kit instructions a needle-like probe 59 is inserted through a rupturable cap 61 piercing the capsule to release its fluid to co-mingle with the receptacle fluid.

Thus, when the disc 34 is rotated to the detent means corresponding to the receptacle 57 the mixed fluid material rains upon the specimen in the manner described previously.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A composite, hand held contamination free personal testing device comprising:
   a support member carrying a plurality of receptacles arranged in arcuate array for containing liquid materials,
   a cutting element operatively connected to said support member,
   said support member and said cutting element being movable relative to one another in a generally horizontal mode whereby said cutting element is operable to slit said receptacles to release said liquid material to flow from said receptacles in a generally vertical direction when relative motion occurs.

2. A composite, hand held contamination free personal testing device comprising:
   a support member carrying at least one receptacle for containing liquid materials,
   said receptacle terminating in a nipple,
   a cutting element operatively connected to said support member,
   said support member and said cutting element being movable relative to one another in a generally horizontal mode whereby said cutting element is operable to shear the nipple from said receptacle to release said liquid to flow from said receptacle in a generally vertical direction when relative motion occurs.

3. A composite, hand held contamination free personal testing device comprising:
   a support member carrying at least one receptacle for containing liquid materials,
   a cutting element operatively connected to said support member,
   said support member and said cutting element being enclosed substantially in a first housing member,
   a second housing member connected to said first housing member by an axle,
   said cutting element being rotatable in a generally horizontal mode about said axle whereby said cutting element is operable to slit said receptacle to release said liquid material to flow from said receptacle in a generally vertical direction when said cutting element rotates about said axle.

4. A composite, hand held contamination free personal testing device comprising:
   a support member carrying at least one receptacle for containing liquid materials,
   a cutting element operatively connected to said support member,
   a cutting element being provided with a slot to receive and to provide clearance for a portion of said receptacle whereby said cutting element is operable to slit said receptacle to release said liquid material to flow said receptacle in a generally vertical direction when said relative motion occurs.

5. A composite, hand held contamination free personal testing device comprising:
   a support member carrying at least one receptacle for containing at least two different, separately contained liquid materials,
   a first liquid being contained within said receptacle and a second liquid being contained within a rupturable capsule means within said receptacle,
   a cutting element operatively connected to said support member, said support member and said cutting element being movable relative to one another in a generally horizontal mode whereby said cutting element is operable to slit said receptacle to release said liquid material to flow from said receptacle in a generally vertical direction when said relative motion occurs.

6. A composite, hand held contamination free personal testing device comprising:
   a support member carrying at least one receptacle for containing liquid materials,
   a cutting element operatively connected to said support member,
   said support member and said cutting element being enclosed substantially in a first housing member,
   said support member and said cutting element being movable relative to one another in a generally horizontal mode whereby said cutting element is operable to slit said receptacle to release said liquid material to flow from said receptacle in a generally vertical direction when relative motion occurs,
   said first housing member being provided with a specimen access opening,
   said first housing member and said cutting element being provided with cooperating detent means for registering said cutting element releasably in a predetermined position relative to said first housing member.

* * * * *